United States Patent
Shriver

(10) Patent No.: US 9,734,400 B2
(45) Date of Patent: Aug. 15, 2017

(54) SYSTEM AND METHOD FOR FIELD VARIANCE DETERMINATION

(71) Applicant: AgriSight, Inc., Ann Arbor, MI (US)

(72) Inventor: John Shriver, Ann Arbor, MI (US)

(73) Assignee: AgriSight, Inc., Ann Arbor, MI (US)

( * ) Notice: Subject to any disclaimer, the term of this patent is extended or adjusted under 35 U.S.C. 154(b) by 0 days.

(21) Appl. No.: 15/012,762

(22) Filed: Feb. 1, 2016

(65) Prior Publication Data

US 2016/0239709 A1 Aug. 18, 2016

Related U.S. Application Data

(60) Provisional application No. 62/109,888, filed on Jan. 30, 2015, provisional application No. 62/130,314, filed on Mar. 9, 2015.

(51) Int. Cl.
G06K 9/00 (2006.01)
G05B 15/02 (2006.01)
G01N 33/02 (2006.01)

(52) U.S. Cl.
CPC ....... G06K 9/00657 (2013.01); G01N 33/025 (2013.01)

(58) Field of Classification Search
None
See application file for complete search history.

(56) References Cited

U.S. PATENT DOCUMENTS

| | | | |
|---|---|---|---|
| 5,497,419 A | 3/1996 | Hill | |
| 6,525,276 B1 | 2/2003 | Vellidus et al. | |
| 6,751,515 B2 | 6/2004 | Moore | |
| 7,031,927 B1 | 4/2006 | Beck et al. | |
| 7,058,197 B1 * | 6/2006 | McGuire | G06K 9/00657 382/100 |
| 7,068,816 B1 | 6/2006 | Knoblauch et al. | |
| 9,113,590 B2 | 8/2015 | Johnson | |
| 9,131,644 B2 | 9/2015 | Osborne | |
| 2001/0036295 A1 * | 11/2001 | Hendrickson | G01J 3/2803 382/110 |
| 2002/0091458 A1 | 7/2002 | Moore | |
| 2003/0028321 A1 | 2/2003 | Upadhyaya et al. | |

(Continued)

FOREIGN PATENT DOCUMENTS

WO 2014120887 A1 8/2014

*Primary Examiner* — Ryan Jarrett

(74) *Attorney, Agent, or Firm* — Jeffrey Schox; Diana Lin

(57) ABSTRACT

A method for measuring performance of a geographic region from an image including a set of image elements includes: receiving the image corresponding to a time unit, generating a geographic region performance map for the image, combining the geographic region performance map with a second geographic region performance map, and generating a geographic region performance summary map. Generating the geographic region performance map for the image can include mapping a set of image elements to a set of geographic sub-regions, generating a set of vegetative performance values for the set of image elements, mapping the set of image elements to a set of crop types, defining a subset of image elements corresponding to a subset of vegetative performance values, comparing vegetative performance values of the subset of vegetative performance values, and generating geographic region performance values for the subset of image elements.

19 Claims, 7 Drawing Sheets

(56) References Cited

U.S. PATENT DOCUMENTS

| | | |
|---|---|---|
| 2004/0077347 A1 | 4/2004 | Lauber et al. |
| 2004/0194442 A1 | 10/2004 | Maertens |
| 2005/0108100 A1 | 5/2005 | Veen et al. |
| 2006/0017551 A1 | 1/2006 | Neher et al. |
| 2007/0038338 A1 | 2/2007 | Larschan et al. |
| 2007/0065857 A1 | 3/2007 | Glaser et al. |
| 2008/0195268 A1 | 8/2008 | Sapilewski et al. |
| 2010/0069035 A1 | 3/2010 | Johnson |
| 2011/0270723 A1 | 11/2011 | O'Neil |
| 2011/0270724 A1 | 11/2011 | Waggoner |
| 2011/0290873 A1 | 12/2011 | Nishiguchi et al. |
| 2012/0101784 A1 | 4/2012 | Lindores et al. |
| 2012/0123817 A1 | 5/2012 | Hohenberger et al. |
| 2012/0237083 A1 | 9/2012 | Lange et al. |
| 2012/0280797 A1 | 11/2012 | Meyers |
| 2013/0226607 A1 | 8/2013 | Woody et al. |
| 2014/0012732 A1 | 1/2014 | Lindores |
| 2014/0205154 A1 | 7/2014 | De et al. |
| 2014/0278645 A1 | 9/2014 | Davidson et al. |
| 2015/0278640 A1 | 10/2015 | Johnson et al. |
| 2015/0278838 A1 | 10/2015 | Rasa et al. |
| 2015/0278966 A1 | 10/2015 | Johnson |
| 2016/0078375 A1 | 3/2016 | Ethington et al. |
| 2016/0078570 A1 | 3/2016 | Ethington et al. |
| 2016/0112362 A1 | 4/2016 | Perazzo et al. |
| 2016/0180473 A1* | 6/2016 | Groeneveld ............ G06Q 50/02 705/7.25 |

* cited by examiner

SYSTEM AND METHOD FOR FIELD VARIANCE DETERMINATION

CROSS-REFERENCE TO RELATED APPLICATIONS

This application claims the benefit of U.S. Provisional Application Ser. No. 62/109,888, filed on 30 Jan. 2015, and U.S. Provisional Application Ser. No. 62/130,314, filed on 9 Mar. 2015, which are incorporated herein in their entireties by this reference.

This application is related to U.S. application Ser. No. 15/012,738 filed 1 Feb. 2016 and titled "SYSTEM AND METHOD FOR CROP HEATH MONITORING", and to those disclosed in related U.S. application Ser. No. 15/012,749 filed 1 Feb. 2016 and titled "GROWTH STAGE DETERMINATION SYSTEM AND METHOD", which are herein incorporated in their entirety by this reference.

TECHNICAL FIELD

This invention relates generally to the precision agriculture field, and more specifically to a new and useful system and method for determining performance baselines for geographic regions in the precision agriculture field.

DESCRIPTION OF THE PREFERRED EMBODIMENTS

Figure 1:
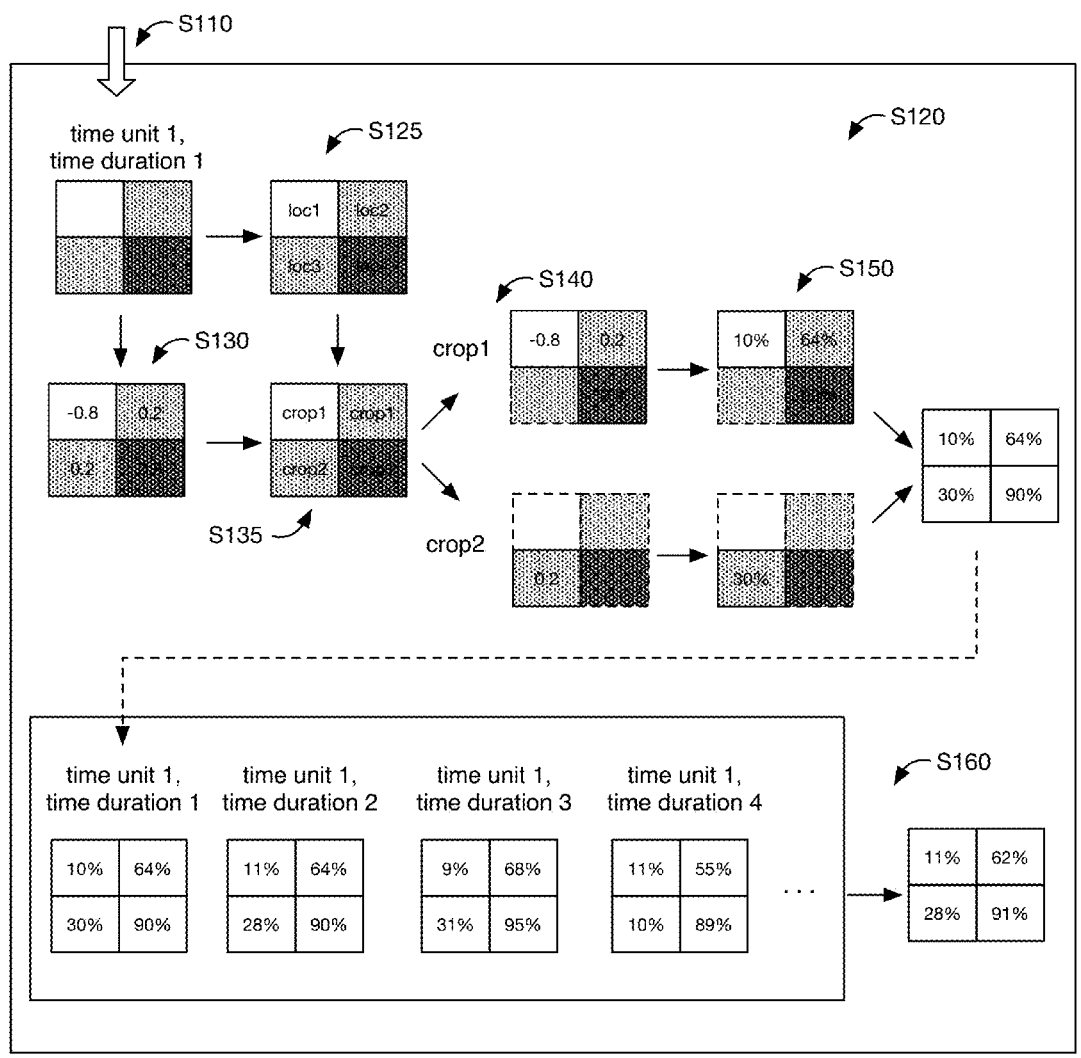
FIG. 1 is a schematic representation of a variation of the method.

The following description of the preferred embodiments of the invention is not intended to limit the invention to these preferred embodiments, but rather to enable any person skilled in the art to make and use this invention.

As shown in FIGS. 1-5, the method 100 for measuring performance of a geographic region from an image including a set of image elements includes receiving the image corresponding to a time unit S110, generating a geographic region performance map for the image S120, and generating a geographic region performance summary map S160 by combining the geographic region performance map with a second geographic region performance map. Generating the geographic region performance map for the image S120 can additionally or alternatively include mapping image elements to geographic sub-regions S125, generating vegetative performance values for the image elements S130, associating crop types with the image elements or geographic sub-regions S135, defining a subset of image elements S140, comparing vegetative performance values associated with the subset of image elements S145, and/or generating geographic region performance values for the subset of image elements S150.

The method 100 can additionally or alternatively include generating a crop input prescription S180 and/or notifying a user S190. The method 100 can additionally or alternatively be repeated for each of a plurality of images of the same geographic region, each image recorded at different time units within a time duration (e.g., recorded at different time units within a growing season or year). The method 100 can additionally or alternatively be repeated for each of a plurality of images of the same geographic region, each image recorded at substantially the same time unit across different time durations (e.g., recorded at substantially the same month or day within a growing season or year). These images can be aggregated and processed to generate summaries of the geographic region variability for the time units, the time durations, and/or any other suitable time period. The method can be performed in real time, near-real time, asynchronously with image generation, or at any other suitable frequency.

The method 100 functions to generate a performance map for the geographic region (e.g., field) during the time duration, and can additionally function to generate a performance summary map for the geographic region over multiple time units, a time duration, and/or multiple time durations. The performance summary map (e.g., yield performance map, yield proxy map) preferably provides an expected field performance for a given recurrent time duration (e.g., recurrent month, time interval during the growing season, GDD, etc.), but can alternatively be used in any other suitable manner. In some variants, this method can function to identify high- or low-performance agricultural fields or portions thereof.

1. Benefits

The method 100 can confer several benefits over conventional methods for measuring performance. First, the method 100 uses remote monitoring data (e.g., satellite images), such that entire crop fields can be analyzed for performance (e.g., yield performance, soil performance, geographic region performance, etc.). This is in contrast with conventional methods, in which only small portions of the crop fields can be sampled for measuring performance.

Second, the method 100 can measure crop field performance in real- or near-real time (e.g., as the remote monitoring data is received). This is in contrast with conventional methods, which can only measure performance after the growing season is over (e.g., by using remotely sensed or otherwise determined data collected over the entirety of the growing season) or when a user affirmatively requests a performance analysis (e.g., when a user physically enters the crop field to check on crop health).

Third, because the method 100 is remotely monitoring the entire geographic region over time, the method 100 can confer the additional benefit of recording and identifying changes in crop field performance over a growing season, multiple growing seasons, and/or any suitable duration of time. These historical geographic region performance metrics captured over time can be leveraged in generating an expected change in performance over time, which can be compared against current changes in performance for identifying crop health anomalies. Identifying crop health anomalies over time can introduce the benefit of recording and identifying anomaly patterns (e.g., geographic coverage pattern, spread pattern, spread rate, etc.). These patterns can subsequently be used to identify the cause of the anomaly, be used to recommend remedial treatment, and/or be used in any other suitable manner.

Fourth, the method 100 can enable a user (e.g., a farmer) to view precision-level maps without providing their own information, develop precision-level prescriptions (e.g., treatments, crops, timing, etc.) to accommodate for differences in field performance, detect crop anomalies, enable growth stage prediction of crops in each field segment, allow growers to manage their fields to optimal potential, and/or enable any other suitable field performance-related functionality. Further, the method 100 can enable the generation of geographic region performance maps with superior image clarity and performance metrics compared to traditional yield maps and soil zone maps.

Fifth, by leveraging remote monitoring data for the entire crop field, the method 100 can normalize performance metrics for a geographic region based on crop types associated with the geographic region. For example, corn fields (e.g., pixels of growing corn) can be compared with corn fields, instead of comparing corn fields to wheat fields. The method 100 can avoid normalizing the parameter value of a first crop (e.g., corn) with a parameter value derived from a second crop (e.g., wheat), which can mask the variation within the population of the first crop. As such, a crop-agnostic performance summary map of the underlying geographic region can be generated based on historical performance values for the field, irrespective of whether the field is currently growing multiple crop types or a single crop type. Because this performance map is generated from the output of the geographic region (e.g., based on the plant performance), the performance map can accommodate for the effects of soil, terrain, sun exposure, weather, groundwater, or any other suitable factor that influences plant growth.

Sixth, the performance map can describe the relative performance of the underlying geographic sub-regions over multiple growing seasons rather than over a single growing season. Such a map can account for variability that might arise when relative performance is only measured within a single growing season (e.g., variability in treatment types or practices, imperfect treatments, pest infection, etc.). Further, by generating a performance map capturing relative performance over a minimum of a predetermined number of years (e.g., five years), the method 100 can account for performance value outliers caused by pests, imperfect treatment application, and/or other anomalies.

2. Method

2.1 Receiving an Image.

As shown in FIGS. 2A-2C, 4, and 5, receiving an image S110 functions to obtain an image indicative of the performance of a geographic region. Receiving an image S110 can additionally or alternatively include processing the image S111 and/or generating an image quality metric for the image S115.

The image is preferably of a geographic region, more preferably of crops in-situ within the geographic region. Alternatively, the image can include a portion of the geographic region (and the plants within the geographic region) and/or areas surrounding the geographic region. However, the image can include any suitable content to be used in measuring the performance of the geographic region. The geographic region can be an agricultural field (e.g., crop field), portion of an agricultural field, multiple contiguous agricultural fields, multiple separate agricultural fields, a region encompassing both agricultural fields and developed land, or be any other suitable geographic region.

The geographic region is preferably a two- or three-dimensional physical region, but can alternatively be one dimensional or be a point (e.g., a geographic location). The geographic region can be predetermined (e.g., by a political entity or a user), dynamically determined (e.g., automatically determined, etc.), or otherwise determined. The geographic region can be defined by a geofence, political boundary, management zone, common land unit, geological features (e.g., mountains, rivers, etc.), buildings, or defined in any other suitable manner. The geographic region can be identified by a geographic coordinate system (e.g., geographic latitude and longitude, UTM and/or UPS system, Cartesian coordinates, etc.), an address, a venue name, a common land unit identifier, a management zone identifier, or by any other suitable unique or non-unique identifier. The geographic region preferably includes geographic sub-regions that constitute the geographic region. However, any other suitable type of sub-unit can be used in constructing the geographic region. The geographic region can be virtually represented within the system by a virtual model (e.g., a virtual map), an array of values (e.g., a value for each geographic sub-region within the geographic region), an identifier (e.g., a location identifier, such as a set of coordinates, a geographic area, a venue name, etc.), or be otherwise virtually represented. A geographic sub-region can be virtually represented within the system by a virtual model (e.g., a subset of the geographic region model), an identifier (e.g., a geographic identifier, a hash value, etc.), or be otherwise virtually represented. Each geographic sub-region virtual representation is preferably associated with a physical geographic sub-region, and can additionally be associated with image elements representing or capturing the respective physical geographic sub-region. Each geographic sub-region virtual representation can be stored in association with one or more sets of: spectral signals extracted from the associated image elements, vegetative performance values calculated from the spectral signals, relative performance metrics calculated from the vegetative performance values (e.g., normalized vegetative performance values), crop types (e.g., one for each growing season), or any other suitable information.

The image can be a two-dimensional image, a one-dimensional image, a three-dimensional image (e.g., generated from two or more images), or have any suitable number of dimensions. The image can be a single image or frame, as captured by the imaging system, or can be a composite image (e.g., mosaic) including multiple images that are stitched together. In variations where the image is a composite image, the individual images constituting the composite image are preferably recorded at substantially the same time unit. Alternatively, the individual images are recorded at different time units. However, the images making up the composite image can be recorded at any suitable time unit or time units over any suitable time duration or time durations. The image can be a still image, a kinetic image (e.g., a video), or have any other suitable kinetic parameter. The image can be a multispectral image, hyperspectral image, ultraspectral image, be an image captured within the visible range, LIDAR-derived image, ultrasound-derived image, radar-derived measurement, or be an image captured any other suitable electromagnetic or acoustic frequency. Alternatively or additionally, a secondary measurement, such as electric conductivity (e.g., soil conductivity or EC), can be recorded by a secondary sensor and used as an image. In a specific example, soil conductivity measurement values recorded over the geographic region (e.g., with a ground-based soil conductivity meter) can be mapped to a virtual representation of the geographic region, correlated with other images of the geographic region, and used in the method. However, any other suitable signal can be emitted and/or recorded to generate the image. The image can be captured and/or received by an aerial system (e.g., satellite system, drone system, etc.), a terrestrial system (e.g., a camera dragged along the field by a tractor), or any other suitable imaging system.

The image is preferably associated with one or more temporal indicators. The temporal indicator can be a time unit relative to a time duration, an absolute time (e.g., indicated by a global timestamp), or any other suitable measure of time. The time duration can be a unique or non-unique time duration. Examples of time durations include a unique year (e.g., 2015), a unique growing season (e.g., spring of 2014, fall of 2009, etc.), a growth stage (e.g., vegetative stage, reproductive stage), relative time duration (e.g., spring, growth duration), or any other suitable time duration. The time unit relative to the time duration can be a time unit within the time duration (e.g., an hour of a day, a day of the week, a day of a month, a day of a year, a week of a year, a month of a year, day of the planting season, growth stage of the growth duration, etc.), or be any other suitable time unit. The time unit can be a recurrent time unit that recurs across multiple time durations (e.g., January of 2015 and January of 2016, Apr. 5 of Spring 2015 and April 5 of Spring 2016, etc.).

The image is preferably received at a remote server that stores and processes the image. Alternatively, the image can be received at a user device, but can additionally or alternatively be received at any suitable component. The image is preferably received from a third-party source (e.g., via a third party service that captured the images), but can be received from a direct source (e.g., directly from an image-taking component, directly from a user device of a grower who captured the image, etc.). However, the image can be received from any suitable entity with any suitable relationship with the component (e.g., remote server) receiving the image.

The image preferably includes a set of image elements. Types of image elements can include a pixel, a superpixel, a digital value, an image segment, or any other suitable image element. Alternatively, the image can be a single image element. However, the image can include any number of image elements defined in any suitable fashion.

In one variation, the image can be a satellite image encompassing one or more agricultural fields. The image can be associated with a timestamp. The timestamp can be a relative timestamp, such as a time unit within a time duration (e.g., 5th measurement of the year, a measurement in Spring, etc.), a global timestamp, such as a unique time (e.g., 2:34 p on May 3, 2012), or be any other suitable timestamp. In one example, the pixel-to-real-world distance (e.g., pixel to real-world meter, pixel to real-world inch, etc.) can be known or estimated based on the satellite height from the field and focal length of the satellite camera. In this example, the image can be divided into a 5 meter by 5 meter grid, where the parts of the method 100 can be performed with respect to the grid.

2.1.A Pre-Processing an Image.

Receiving an image S110 can include pre-processing an image S111, which functions to condition the image for generating a geographic region performance map based on the conditioned image. Processing the image preferably includes spectral band adjusting, where bands of the image are adjusted and registered to other bands of the image. Additionally or alternatively, image processing can include compensating for variation in shadows resulting from topography variance and/or aerial imagery captured at different times of day. However, image processing can additionally or alternatively include other types of image processing including: image sharpening, image smoothing, photo manipulation, brightness adjustments, and/or any other suitable type of image processing. The image can be processed at a remote server, but can alternatively be processed at a user device and/or any other suitable entity.

In one variation, pre-processing an image includes processing the image with respect to other images of an image set. For example, each image of the set can be calibrated with respect to the remaining images of the set in order to enable accurate comparison of fields irrespective of variance in the time of day at which the images were captured.

2.1.B Generating an Image Quality Metric.

Figure 5:
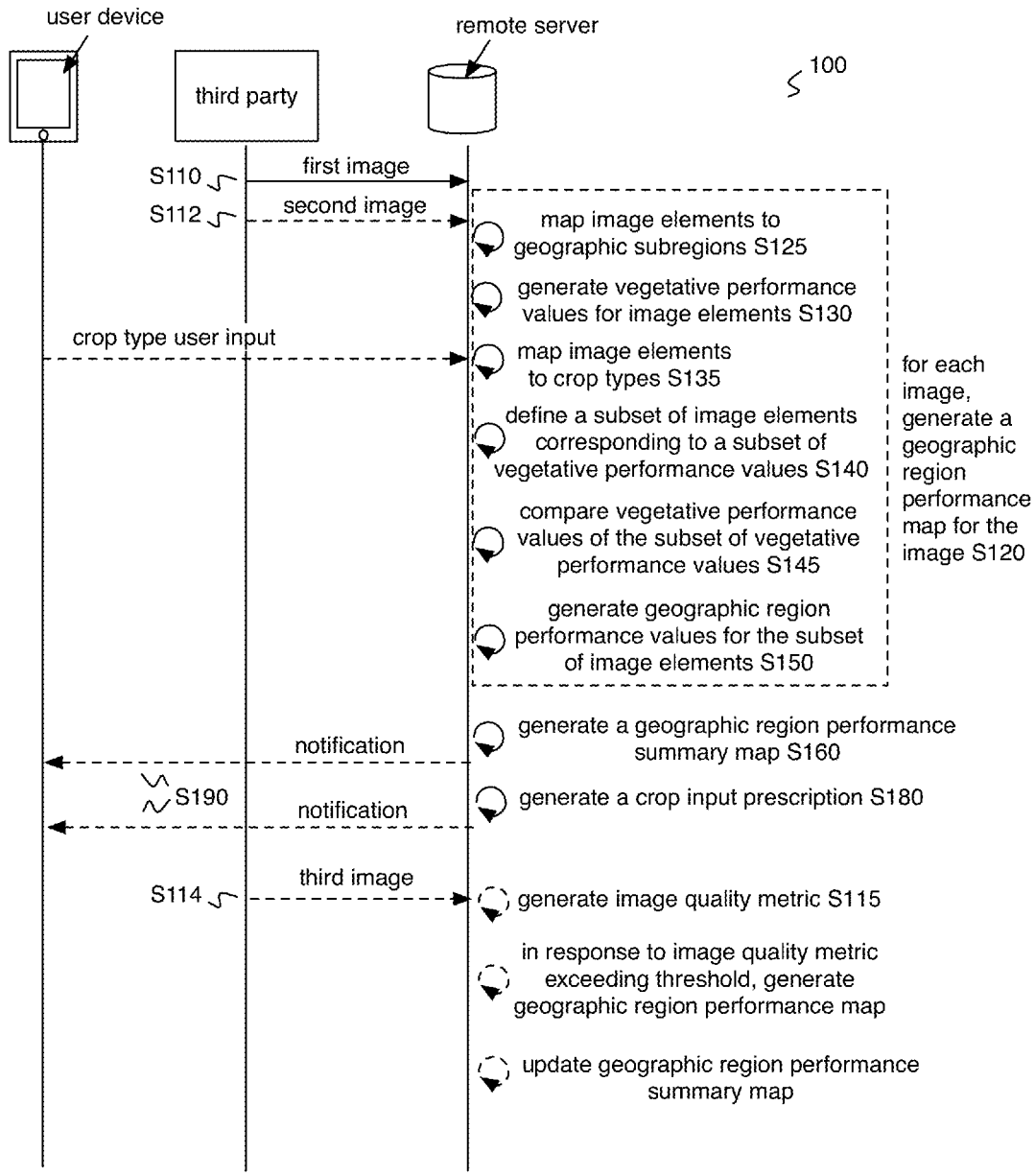
FIG. 5 is a schematic representation of a variation of the method.

As shown in FIG. 5, receiving an image S110 can include generating an image quality metric for the image S115, which functions to calculate a metric measuring a suitability of the image for use in evaluating performance of a geographic region. The image quality metric can be used in determining whether to include or exclude the image from a pool of viable images to be used in evaluating geographic region performance. For example, if the image quality metric is below a specified image quality metric threshold, the image can be excluded from further processing and analysis, such that the image will not be included in evaluating the performance of the geographic region. If the image quality metric exceeds a threshold image quality metric, a geographic region performance map can be generated for the image. Additionally or alternatively, the image quality metric can be used in combining geographic region performance maps S160, such as by giving a lower weight to a geographic region performance map generated from an image with a lower image quality metric. However, the image quality metric can be additionally or alternatively used in other portions of the method 100 including at least S120 and S160, and/or can be used in any other suitable process. An image quality metric can be generated for each image of a set of images. Additionally or alternatively, an image quality metric can be generated for the set of images (e.g., a single metric describing the quality of the set). However, image quality metrics can be generated for any number or combination of images. An image quality metric can be generated for an image after receiving the image S110 and prior to generating a geographic region performance map for the image S120. However, the image quality metric can be generated at any time prior, in conjunction with, or after any suitable portion of the method 100.

Generating the image quality metric can include generating the image quality metric based on an amount of cloud coverage present in the image. Cloud coverage and the image quality metric preferably have a negative correlation, such that an increased amount of cloud coverage results in a decreased image quality metric value. However, cloud coverage and the image quality metric can have any suitable relationship. In one variation, cloud coverage can be measured as a percentage of the image covered in clouds. For example, a probabilistic model can be employed for an image to generate masks for portions of the image, where the masks indicate an obscured geographic sub-region (e.g., obscured by clouds). The percentage of the image covered in a generated mask can correspond to the percentage of the image covered in clouds. If the cloud coverage percentage exceeds a specified cloud coverage threshold, the image can be filtered out from further analysis. Alternatively, if the severity of cloud coverage exceeds a threshold severity for a given image segment, the image segment can be masked. However, exclusion of images and/or masking of image segments can be based on any other suitable criteria. In another variation, cloud coverage can be measured as a degree of cloud coverage covering the geographic region at an image element (e.g., a high amount of cloud coverage at a certain pixel). However, cloud coverage can be measured with any suitable unit of measurement or combination of units of measurement.

Other criteria in determining an image quality metric can include: image resolution, image blurriness, amount of the geographic region present in the image, weather anomalies, user input (e.g., a user indication that an image is unrepresentative of the geographic region), time unit corresponding to the image, soil parameters, crop type, and/or any other suitable criteria.

2.2 Generating a Geographic Region Performance Map.

As shown in FIGS. 2B and 3-5, generating a geographic region performance map S120 functions to measure performance of geographic sub-regions of the geographic region at a time unit. Generating the geographic region performance map S120 can additionally or alternatively include mapping image elements to geographic sub-regions S125, generating vegetative performance values S130, mapping image elements to crop types S135, defining a subset of image elements S140, comparing vegetative performance values S145, and generating geographic region performance values S150. The geographic region performance map is preferably a virtual model representing the crop performance of each of a set of geographic sub-regions (e.g., an array of values, etc.), but can alternatively be a virtual map representative of the crop performance at each virtual position corresponding to each of a set of geographic sub-regions, or be any other suitable virtual representation of the geographic region performance.

The geographic region performance map is preferably generated performed at a remote server, but can alternatively be performed at a user device and/or by any other suitable entity. Generating the geographic region performance map S120 can be entirely performed at a single component (e.g. at a remote server), but can alternatively be performed modularly, with portions of S120 performed at a first component (e.g., at a remote server), and other portions of S120 performed at a second component (e.g., at a user device). Images with an image quality metric exceeding an image quality metric threshold can each be used to generate individual geographic region performance maps for the images. Alternatively, geographic region performance maps can be generated for each image of a set of received images regardless of whether an image quality metric has been generated for the image, and if an image quality metric was generated for the image, regardless of the image quality metric value. A single geographic region performance map can be generated for an image. Alternatively, multiple geographic region performance maps (e.g., different maps generated by different means, different maps covering different areas of the geographic region, different maps indicating different performance metrics, etc.) can be generated for a single image. However, a single geographic region performance map can be generated for multiple images, and any number or combination of geographic region performance maps can be generated for any number or combination of images.

The geographic region performance map can be generated based on vegetative performance values (e.g., WDRVI values) corresponding to image elements of the image. Additionally or alternatively, the geographic region performance map can be generated based on supplemental data including soil data (e.g., soil texture, soil hydraulic properties, soil organic matter, etc.), weather data (e.g., daily temperature, precipitation, radiation, etc.), and/or crop management data (e.g., user-inputted data, historic seeding prescriptions, etc.). However, the geographic region performance emap can be generated based on any suitable data. The geographic region performance map can indicate the absolute or relative crop performance (e.g., indicative of crop yield) at a given time unit for each geographic sub-region of the geographic region, where the time unit is the time unit at which the image received in S110 was captured. Additionally or alternatively, the geographic region performance map can indicate absolute or relative performance characteristics of soil, a crop, a crop input (e.g., seeding prescription, nitrogen prescription, etc.), and/or any other suitable entity.

Generated geographic region performance maps can be stored and thereafter used as a baseline for comparison with newly generated geographic region performance maps. Additionally or alternatively, the geographic region performance maps can be used in enabling growth stage prediction of crops in field segments. The geographic region performance maps can additionally or alternatively be used in any manner analogous to those disclosed in related U.S. application Ser. No. 15/012,738 filed 1 Feb. 2016 and titled "SYSTEM AND METHOD FOR CROP HEATH MONITORING", and to those disclosed in related U.S. application Ser. No. 15/012,749 filed 1 Feb. 2016 and titled "GROWTH STAGE DETERMINATION SYSTEM AND METHOD", which are herein incorporated in their entirety by this reference.

2.2.A Mapping Image Elements to Geographic Sub-Regions.

Figure 2A:
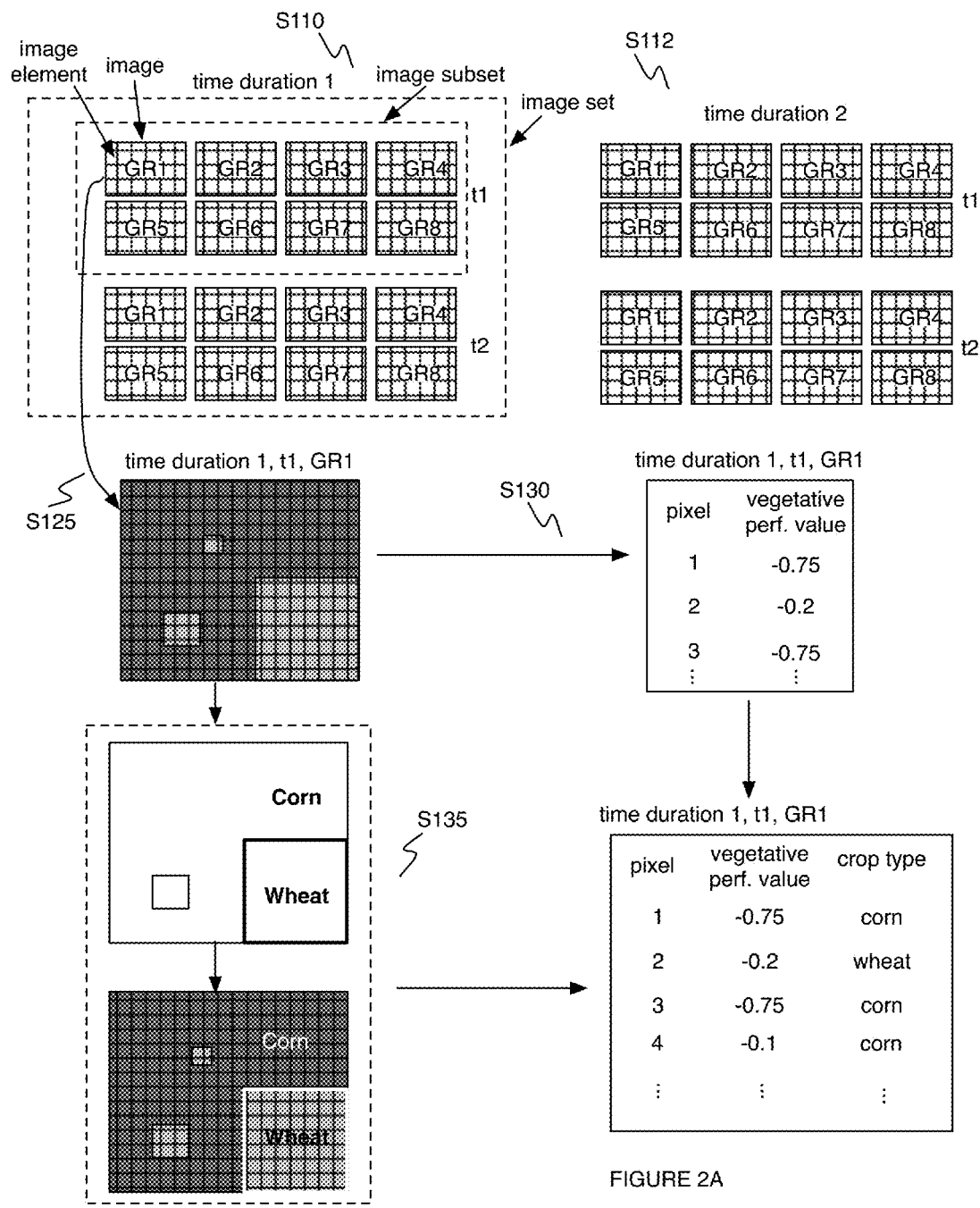
FIGS. 2A to 2C are schematic representations of a specific example of a method for measuring performance of a geographic region.
Figure 4:
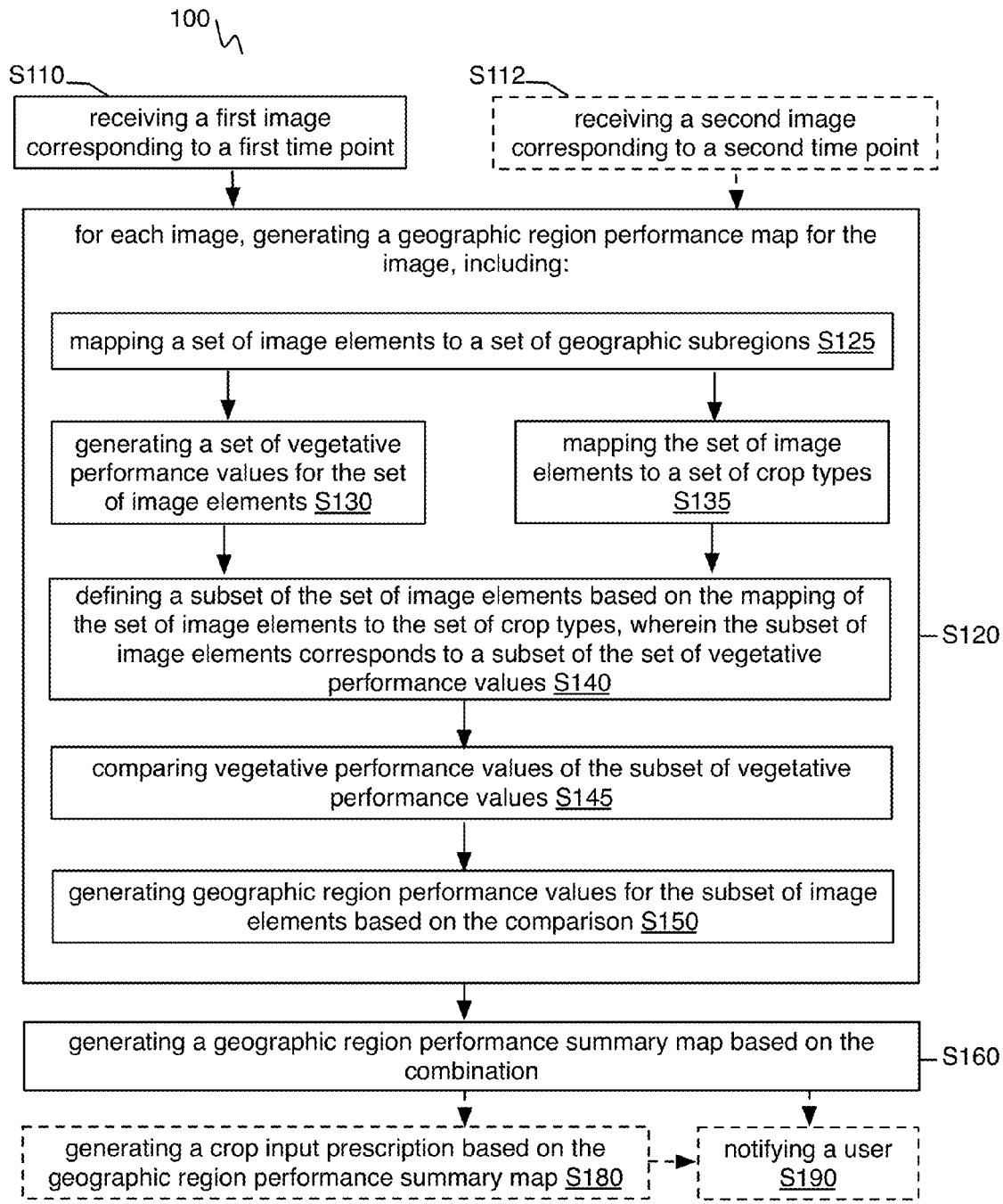
FIG. 4 is a schematic representation of a variation of the method.

As shown in FIGS. 2A and 4-5, generating a geographic region performance map S120 can include mapping image elements to geographic sub-regions S125, which functions to correlate image elements of the received image to geographic sub-regions of the geographic region. Geographic sub-regions are preferably encompassed within the geographic region, but can alternatively be separated from the geographic region or partially encompassed by the geographic region. However, image elements can be mapped to any combination of geographic sub-regions lying within, partially within, or outside the geographic region. The geographic sub-regions can possess characteristics of a type that the geographic region can possess (e.g., can be an agricultural field, developed land, single or multi-dimensional, predetermined, dynamically determined, etc.). Alternatively, the geographic sub-regions can possess characteristics exclusive of those capable of being possessed by the geographic region. However, the geographic sub-regions and the geographic region can exhibit any suitable trait for defining a region upon which performance can be assessed.

Image elements can be mapped to geographic sub-regions S125 based on correspondence of the image element with a geographic coordinate (e.g., geographic latitude and longitude, UTM and/or UPS system, Cartesian coordinates, etc.), an address, a venue name, a common land unit identifier, a management zone identifier, or by any other suitable unique or non-unique identifier. Additionally or alternatively, mapping image elements to geographic sub-regions S125 can be based on previously received images that have had their image elements mapped to geographic identifiers that are present in the geographic region of the current image. Further, the mapping can additionally or alternatively be performed based on user input associating sections of the received image to geographic sub-regions. However, image elements can be mapped to geographic sub-regions in any suitable fashion.

Each image element of the set is preferably mapped to a geographic sub-region. Each image element is preferably mapped to a separate and discrete geographic sub-region from the remainder of the image element set, but can alternatively be mapped to the same geographic sub-region as another image element of the set, be mapped to a geographic sub-region overlapping with the geographic sub-region corresponding to another image element of the set, or be mapped to any other suitable geographic sub-region or set thereof. However, any number or combination of image elements can be mapped to any number or combination of geographic sub-regions (e.g., in a 1:1 relationship, in a greater than 1 to 1 relationship, in a 1 to greater than 1 relationship, etc.).

In a first variation, image elements are mapped to geographic sub-regions in a manner enabling the image elements to be characterized in relation to other image elements based on their respective correspondences with geographic sub-regions. In this variation, a first image element can be mapped to a first geographic sub-region, and a second image element can be mapped to a second geographic sub-region based on: the relationship between the first and second image elements in the image and the mapping between the first image element and the first geographic sub-region. For example, a first geographic sub-region corresponding to a first image element can be characterized as located immediately west of a second geographic sub-region, enabling a second image element to be mapped to the second geographic sub-region based on the second image element's relationship to the first image element. Geographic sub-regions and image elements of a given image are preferably capable of being characterized in relation to geographic sub-regions and image elements of other images, irrespective of whether the geographic sub-regions of the other images are present in the given image. However, the mapping of image elements to geographic sub-regions S125 can enable any suitable characterization of image elements and/or geographic sub-regions in relation to any other image elements and/or geographic sub-regions.

In a second variation, associating an image element with a geographic sub-region (or geographic location) can include: determining a geographic location associated with a reference point on the image (e.g., the upper right corner of the image, image center, etc.), determining a relationship between the image element and the reference point (e.g., three pixels to the right of the reference point), determining a physical geographic distance corresponding to a relationship unit (e.g., each pixel width represents a geographic distance of 5 m), determining the geographic location represented by the image element based on the relationship and physical geographic distance corresponding to the relationship unit (e.g., the image element is associated with the geographic sub-region having a location 15 m to the right of the geographic location associated with the reference point). The geographic location associated with the reference point on the image can be determined based on: the location of the image-capturing device when the image was recorded, the timestamp of the image and the image-capturing device trajectory, landmarks appearing within the image, or otherwise determined. The physical geographic distance corresponding to a relationship unit can be determined based on the field of view of the image-capturing device, the distortion of the image-capturing device, or be otherwise determined.

In a third variation, the image is received from the image source with all image elements pre-associated with a geographic location and/or geographic sub-region identifier. However, image elements can be otherwise mapped to geographic sub-regions.

2.2.B Generating Vegetative Performance Values.

As shown in FIGS. 2A and 4-5, generating a geographic region performance map S120 can include generating vegetative performance values S130, which functions to generate a measure of vegetative performance across the geographic region captured by the image. The plant parameters can additionally or alternatively be used to calibrate, generate, apply, or otherwise use a deterministic model (e.g., DSSAT, WOFOST, APSIM, etc.) to the geographic region. The plant parameters, more preferably the vegetative performance values, can be extracted before image segmentation by crop type, after image segmentation by crop type, or be extracted at any other suitable time. The vegetative performance values preferably indicate the crop performance at a given time unit for a geographic sub-region of the geographic region, where the time unit is the time unit at which the image received in S110 was captured. Additionally or alternatively, the vegetative performance values can indicate performance characteristics of soil, a crop input (e.g., seeding prescription, nitrogen prescription, etc.), and/or any other suitable variable for the geographic sub-region. However, the vegetative performance value can measure any suitable characteristic of a geographic sub-region, geographic region, and/or any suitable area at any relevant time unit.

The plant parameter can be a physiological measurement, morphological measurement, or any other suitable parameter descriptive of one or more plants. Physiological measurements can include vegetation indices (e.g., vegetative performance values), chemical measurements, or any other suitable physiological measurements. Vegetative indices can include Normalized Difference Vegetation Index (NDVI), Wide dynamic range vegetation index (WDRVI), Transformed Chlorophyll Absorption in Reflectance Index normalized by Optimized Soil-Adjusted Vegetation Index (TCARI/OSAVI), Normalized Difference Red Edge Index (NDRE), Canopy Chlorophyll Content Index (CCCI), Photochemical Reflectance Index (PRI), crop water stress index (CWSI), canopy temperature less air temperature (Tc-Ta), stomatal conductance (G), stem water potential, water stress, water content, Water Band Index (WBI), plant uniformity across the geographic area, Leaf Area Index (LAI), Net Assimilation Rate (NAR), Relative Growth Rate (RGR), Leaf Area Ratio (LAR), Leaf Area Duration (LAD), Crop Growth Rate (CGR), vegetative performance value change over time, vegetative performance value change rate, absolute growth rate in volume, absolute growth rate in number, absolute growth rate in mass, plant density over the geographical region, and/or any other suitable vegetative or plant index or combination thereof.

Generating the vegetative performance values can include measuring the signal from one or more spectral channels (e.g., visual signal, intensity of one or more wavelengths, etc.), processing the image through image processing techniques (e.g., extracting points of interest, gradients of interest, or any other suitable image feature of interest), or otherwise extracting a parameter value from the image. The vegetative performance value can be extracted for a pixel of the image, for a sub-region of the geographic region within the image field of view (e.g., where each pixel can be mapped to a predetermined geographic area based on a known or estimated height of the imaging system and focal length of the imaging system), for the entire image, or for any suitable image element.

A set of vegetative performance values can be generated for a set of image elements of the image received in S110, such that a vegetative performance value is generated for each image element of the set of image elements. Alternatively, vegetative performance values can be generated only for a subset of the image elements of the image. However, any number or combination of vegetative performance values can be generated for any number or combination of image elements (e.g., in a 1:1 relationship, in a greater than 1 to 1 relationship, in a 1 to greater than 1 relationship, etc.). In the variation where vegetative performance values are generated for only a subset of the image elements, selecting image elements for which to generate a vegetative performance value can be based upon image characteristics (e.g., image quality at the image element), weather characteristics (e.g., cloud coverage over a geographic sub-region), soil characteristics (e.g., soil health at a geographic sub-region), crop type (e.g., generating vegetative performance values only for geographic sub-regions growing corn as opposed to other crop types), crop inputs (e.g., generating vegetative performance values only for the geographic regions undergoing a specified seeding regimen or prescription), and/or any other suitable characteristics.

2.2.C Mapping Image Elements to Crop Types.

As shown in FIGS. 2A and 4-5, generating a geographic region performance map S120 can include mapping image elements to crop types S135, which functions to segment the image by crop type, such that commodities can be masked out. Additionally or alternatively, image elements corresponding to cloud coverage, crop health anomalies, or other aberrations can be masked out. The image can be segmented into substantially contiguous regions, each associated with a single crop type of a set of crop types. Alternatively or additionally, a region can be associated with multiple crop types from the set of crop types, and/or different regions can be associated with different crop types from the set of crop types. However, the image can be otherwise segmented. This enables corn fields (e.g., pixels of growing corn) to be compared with corn fields, instead of comparing corn fields to wheat fields. This segmentation can be desirable because different crop types can exhibit different vegetative performance values at a given growth stage or time unit. Because the image can encompass multiple crop types within its field of view, normalizing the parameter value of a first crop (e.g., wheat) with a parameter value derived from a second crop (e.g., corn) can mask the variation within the population of the first crop. For example, for corn and wheat fields that are planted at substantially the same time, corn can exhibit a WRDVI frequency pattern that is strongly positively skewed with a mode of approximately −0.75 at a first time (e.g., May), while the wheat can exhibit a WRDVI frequency pattern that is substantially uniform with a mode of approximately −0.02 at the first time. Normalizing the wheat WDRVI values with a normalization factor derived from corn WDVRI values would mask the WDRVI variation within the wheat population. The segments preferably encompass a plurality of image elements (e.g., pixels, sub-regions, grid units, etc.), but can alternatively encompass a single image element or be a portion of the image element.

Each image element is preferably mapped to a crop type, classified as not corresponding to a crop type, and/or classified as not corresponding to any crop type. Alternatively, some image elements of the received image can forego classification into a crop type. However, any number or combination of image elements can be mapped to any number or combination of crop types (e.g., in a 1:1 relationship, in a greater than 1 to 1 relationship, in a 1 to greater than 1 relationship, etc.). For each image element that is mapped to a geographic sub-region as in S125, a vegetative performance value can be generated for that image element as in S130, and that image element is mapped to a crop type as in S135. However, for a given image element, any suitable combination of portions of the method 100 can be performed for the image element and in any suitable order.

In a first variation, mapping image elements to crop types can include identifying a geographic sub-region associated with a crop type; identifying an image element corresponding to the geographic sub-region; and associating the image element to the crop type. Identifying a geographic sub-region associated with a crop type can include: overlaying a predetermined map of crop types for the geographic region over a virtual map of the geographic region; overlaying a predetermined map of crop types for the geographic region over the image based on the association between the image geographic location and a geographic location associated with the predetermined map; or otherwise identifying the type of crop currently growing on the geographic sub-regions of the geographic region.

The predetermined map can be automatically retrieved from a remote reporting system, automatically generated based on the image, received from a user, automatically determined by a precision agriculture system, or be otherwise determined. In a first example, the map from the remote reporting system can be the cropland data layer corresponding to the time duration. In a second example, the map from the remote reporting system can be a soil survey layer. In a third example, the map can be automatically generated based on the image by matching the plant parameter pattern for the geographic sub-regions over time with a known plant parameter pattern for the crop. In a fourth example, a crop type user input can be received, where the crop type user input associates a crop type to a geographic region or sub-region. The map can be a set of management regions or zones received from a farmer, where the farmer can define fields and assign crops to each field. In a fifth example, the precision agriculture system can generate the map on a per-plant or per-sub-region basis, where the system can automatically determine the position and crop type for each plant as it passes by the plant. In a sixth example, the system can automatically determine the crop type for each geographic sub-region based on the crop growth pattern (e.g., greening parameters over the course of the growing season). However, the image can be segmented according to crop type in any other suitable fashion.

In a second variation, mapping image elements to crop types S135 can include automatically classifying the image elements with a crop type, based on the visual signal of the image itself (e.g., the intensity of a set of wavelengths). Classifying the image elements can include processing the image and analyzing the image to classify an image element. Processing the image can include segmenting the image wherein the image elements within each segment preferably share similar characteristics (e.g., similarities in color, quality, objects represented by the image segments, image element characteristics, etc.), or otherwise processing the image. Analyzing the image can include classifying the image segments as corresponding to a specific crop type (e.g., wheat, corn, etc.), such that image elements contained by a given image segment will be mapped to the crop type or crop types corresponding to the image segment. The image segment can be classified based on characteristic values (feature values) of the image segment (e.g., shape, normalized percentile, etc.), characteristic values of the image elements within the segment (e.g., number, normalized percentile distribution, etc.), or be otherwise classified. The image segment can be classified using a classification module (e.g., applying classification algorithms), regression module, or any other suitable module. However, the image can be processed and/or analyzed in any suitable manner in mapping image elements to crop types S135.

2.2.D Defining a Subset of Image Elements.

Figure 2B:
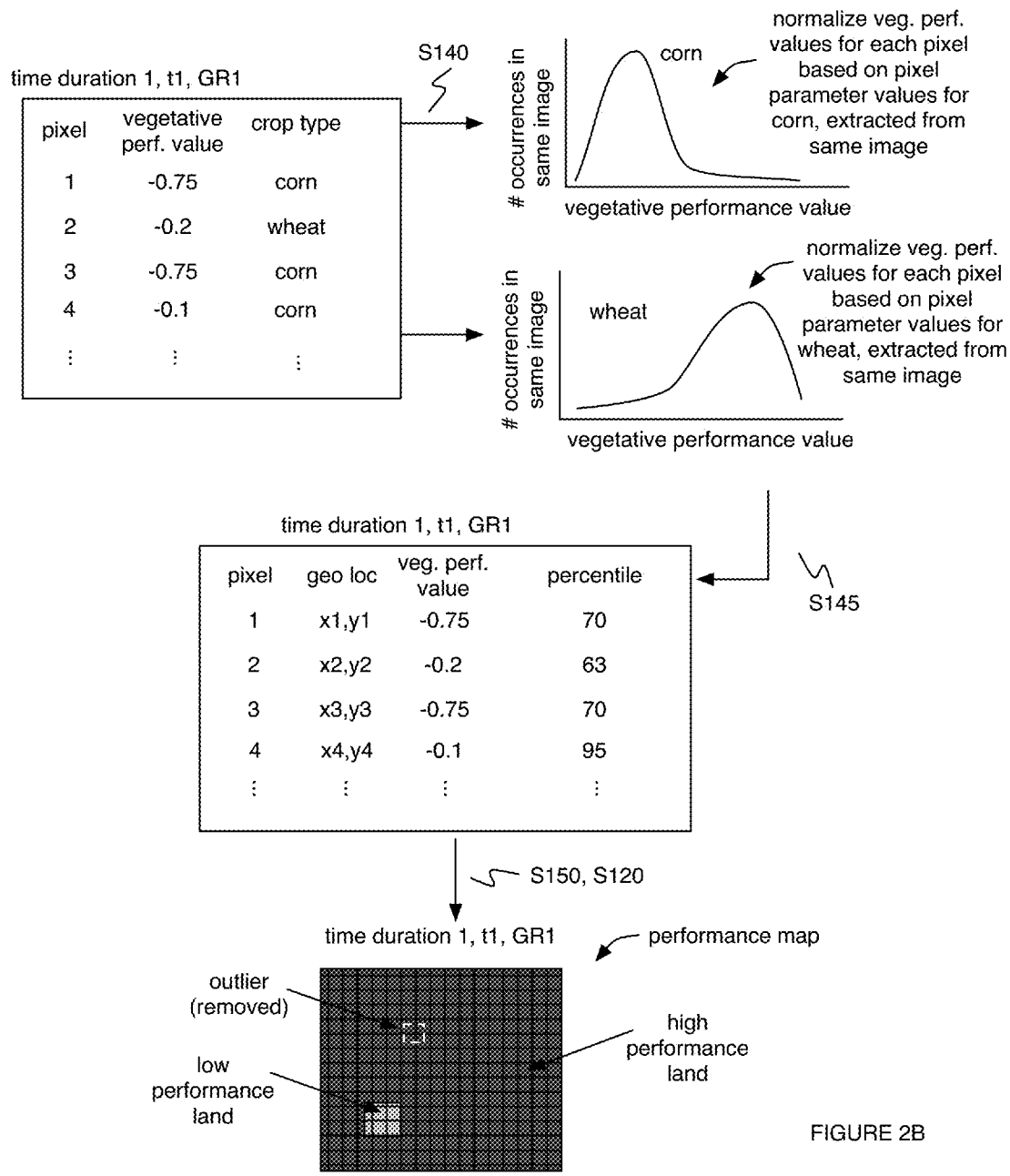
Figure 2C:
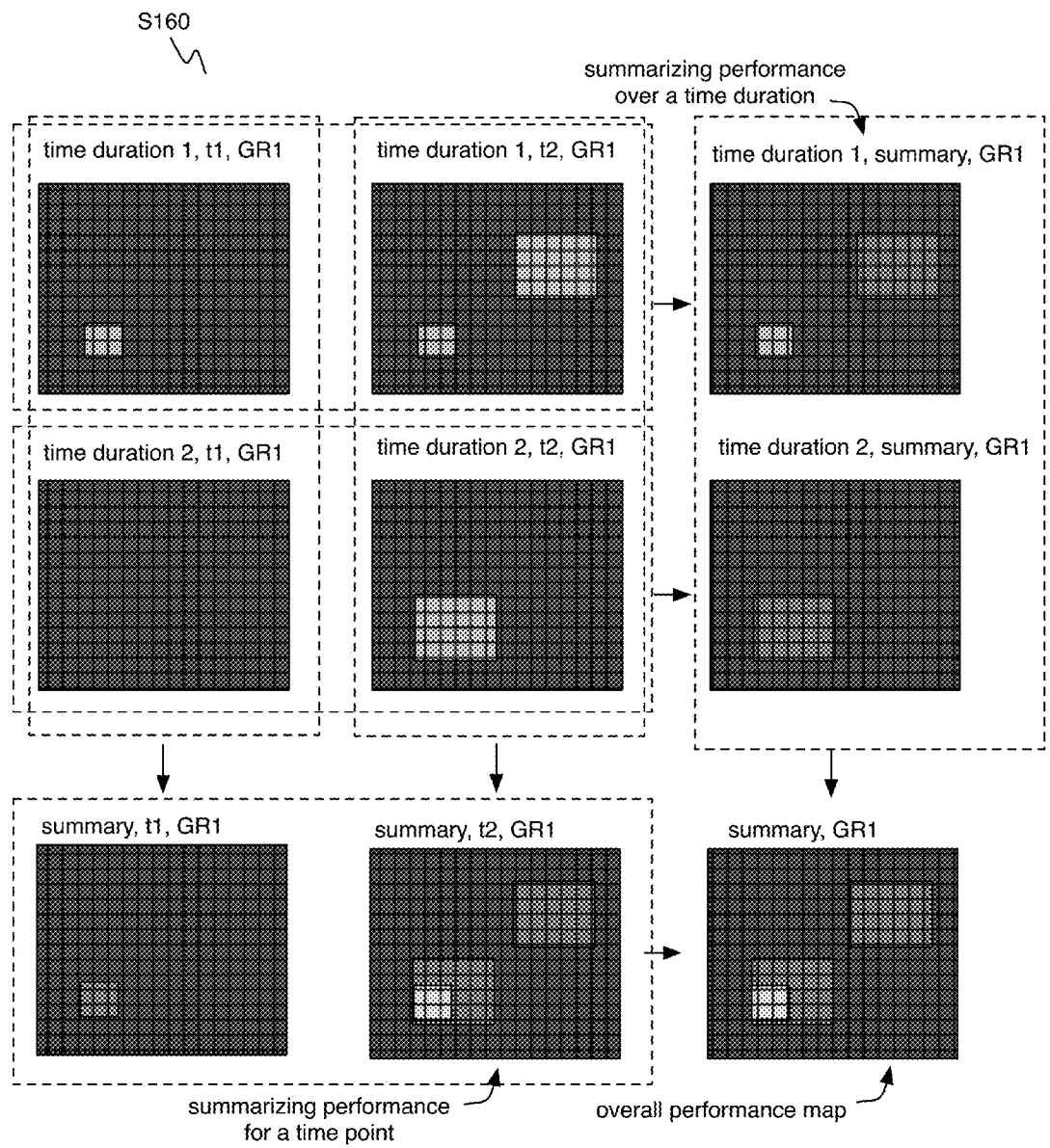

As shown in FIGS. 2B and 4-5, generating a geographic region performance map S120 can include defining a subset of image elements S140, which functions to identify related image elements for comparison to generate the crop- and/or treatment-agnostic metric. The defined subset of image elements is preferably a subset of the set of image elements corresponding to the image received in S110, but the subset of image elements can include any suitable image element. The subset of image elements is preferably defined after crop types have been assigned to the image elements. The subset of image elements is preferably defined after crop types have been assigned to the image elements, and after a set of vegetative performance values have been generated for the image elements. However, S140 can be performed prior to or after any suitable portion of the method 100. However, any number and/or combination of image elements can be mapped or not mapped to any number and/or combination of crop types, and can correspond to any number and/or combination of vegetative performance values.

In a first variation, defining the subset of image elements is based upon crop type. Every image element of the subset of image elements is preferably mapped to a single crop type of the set of crop types. For example, each image element of the subset of image elements can correspond to the crop type of corn. Further, the subset of image elements can constitute all image elements mapped to the given crop type (e.g., for an image, all of the image elements associated with the crop type of corn). The number of defined subsets of image elements for the image will preferably match the number of crop types present in the image (e.g., two defined subsets of image elements if the only crop types present in the image are corn and wheat). Alternatively, the number of defined subsets of image elements can vary from the number of crop types present in the image, but any number of subsets of image elements can be defined in relation to the number of crop types in the set of crop types. Additionally or alternatively, a single subset of image elements can be mapped to a combination of different crop types of the set of crop types (e.g., the subset image elements can constitute each image element corresponding to corn and/or wheat, but not include image elements corresponding to other crop types), but can also be mapped to any number (e.g., 0) and/or combination of crop types.

In a second variation, defining the subset of image elements is based upon vegetative performance values. For example, the criteria for including an image element in the subset of image elements can be dependent on vegetative performance values exceeding a threshold value, being below a threshold value, being within a range of vegetative performance values, being a specific vegetative performance value, and/or any other criteria with respect to vegetative performance values.

In a third variation, defining the subset of image elements can be based upon crop types and vegetative performance values. Defining a subset of image elements can be based upon the criteria of corresponding to a specific crop type and vegetative performance value characteristic. For example, a subset of image elements can be defined as image elements mapped to corn, and with a vegetative performance value exceeding a value of −0.2. However, the subset of image elements can be selected based on any suitable number and/or combination of crop characteristics, vegetative performance characteristics, and/or other characteristics (e.g., soil characteristics, weather characteristics, crop input characteristics, image characteristics, etc.).

2.2.E Comparing Vegetative Performance Values.

As shown in FIGS. 2B and 3-5, generating a geographic region performance map S120 can additionally include comparing the vegetative performance value with a reference performance value S145, which functions to assess the relative vegetative performance for the current growing season. This can be performed prior to normalization, during normalization, or after normalization. The reference performance value is preferably indicative of expected performance for the geographic subregion, but can alternatively be indicative of a preferred performance for the geographic subregion or be indicative of any other suitable performance. The reference performance value is preferably determined based on historic vegetative performance values for a geographic area (e.g., vegetative performance values associated with times before the first time, times before the instantaneous time, times before the instantaneous growing season, etc.), but can alternatively be determined based on new vegetative performance values (e.g., vegetative performance values associated with the first image), market predictions, a reference value received from a user, or be otherwise determined. The geographic area can be the geographic sub-region, geographic region, adjacent geographic region or any other suitable geographic location. Examples of the reference performance value include: a single historic vegetative performance value, an average, mode, and/or median vegetative performance value generated from a set of vegetative performance values, a predetermined value, a dynamically determined value, an automatically determined value, a user-inputted value, or any other suitable value. However, the reference performance value can be any suitably determined composite and/or individual vegetative performance value. Vegetative performance values of a single type (e.g., WDRVI) are preferably compared to vegetative performance values of the same type, but can additionally or alternatively be compared to vegetative performance values of different types.

In a first variation, comparing the vegetative performance value with a relative performance value includes ranking the vegetative performance values. In this variation, the relative performance value can be a prior relative performance value recorded during the same growing season. For example, a relative ranking of vegetative performance values of the subset of image elements can be determined, depending on the respective vegetative performance value. Alternatively, ranking vegetative performance values can be based on absolute magnitude of vegetative performance values, variation in vegetative performance value, and/or any other characteristics of the vegetative performance values. However, vegetative performance values corresponding to the subset of image elements can be compared in any suitable manner.

In a second variation, comparing the vegetative performance value with a relative performance value includes calculating the difference between the vegetative performance value and the reference performance value. In this variation, the reference performance value can be a summary of historic vegetative performance values for the geographic region (e.g., an average of the historic vegetative performance values for the region), a vegetative performance value for a different geographic sub-region captured in the same image (e.g., a geographic sub-region corresponding to the same crop type associated with the non-reference vegetative performance value), or any other suitable type of reference performance value. In one example, calculating the difference can include subtracting an average reference performance value (e.g., averaged from historic vegetative performance values for the geographic region) from the vegetative performance value. In a second example, calculating the difference can include dividing the difference by an average performance value (e.g., averaged from historic vegetative performance values associated with a recurring time unit from a previous growing season).

In a third variation, comparing the vegetative performance value with a relative performance value includes smoothing the vegetative performance value. In this variation, vegetative performance values can be smoothed based on vegetative performance values associated with neighboring image elements, non-neighboring image elements, image elements from other images, images, predetermined values, dynamically determined values, automatically determined values, and/or any other suitable performance values. Alternatively, vegetative performance values can be smoothed based on other types of performance values (e.g., geographic region performance values). Smoothing techniques that can be performed include: linear filtering, adaptive filtering, Gaussian smoothing, moving average, Laplace smoothing, exponential smoothing, and/or any other suitable type of smoothing. The set of vegetative performance values to be smoothed can include any number and/or combination of vegetative performance values. In one example, Gaussian smoothing is performed with respect to a vegetative performance value and the immediately adjacent vegetative performance values associated with a single image. In another example, smoothing is performed with respect to vegetative performance values for the same geographic sub-region, each vegetative performance value associated with a different image captured at a different time. However, smoothing the vegetative performance value can otherwise be performed.

2.2.F Generating Geographic Region Performance Values.

As shown in FIGS. 2B and 3-5, generating a geographic region performance map S120 can include generating geographic region performance values S150, which functions to generate a crop- and/or treatment-agnostic metric to measure land performance. Generating geographic region performance values S150 is preferably based upon comparing vegetative performance values as in S145, but can additionally or alternatively be based upon any other suitable characteristic (e.g., soil characteristics, weather characteristics, crop type, crop input, user-defined criteria, etc.) or analysis of characteristics. The geographic region performance value can be numerical (e.g., 0.5, 78%, etc.), categorical (e.g., low performance, medium performance, high performance), visual (e.g., red color for low performance, yellow color for medium performance, green color for high performance), and/or auditory, but can be of any suitable format or combination of formats.

The performance of the geographic sub-region can directly and/or indirectly indicate or correlate with performance of yield, soil, crop, crop input, and/or any other suitable parameter. However, the geographic region performance value can additionally or alternatively indicate performance of the entire geographic region, surrounding geographic regions, and/or any other suitable area at any given time unit or time duration. Geographic region performance values are preferably calculated for each subset of image elements defined in S140, such that each image element of each subset of image elements corresponds to a geographic region performance value, thereby constituting a geographic region performance map for the geographic region. Alternatively, geographic region performance values are generated only for a defined selection of image elements of the subset of image elements. For example, geographic region performance values can be calculated based on the comparison of vegetative performance values in S145, where geographic region performance values will only be calculated for image elements corresponding to vegetative performance values exceeding a threshold vegetative performance value. However, any number and/or combination of geographic region performance values can be generated for any number and/or combination of image elements present in the received image and/or other images (e.g., in a 1:1 relationship of geographic region performance values to image elements, a greater than 1 to 1 relationship, a 1 to greater than 1 relationship, etc.).

2.2.F.i Normalizing Parameter Values.

In a first variation, generating geographic region performance values S150 can include normalizing (e.g., through L1 normalization, L2 normalization, etc.) the parameter values (e.g., vegetative performance values). This can additionally or alternatively function to rescale any outlying image element values to the same set range as the other image elements of the population, without skewing the image element value distribution. Normalizing the parameter values can reduce or eliminate the need for outlier identification and/or removal. Normalized parameter values can be further processed to generate geographic region performance values. For example, normalized parameter values can be mapped to geographic region performance values possessing a different format for display to a user (e.g., visual geographic region performance values of red, yellow, and green geographic areas corresponding to "low," "medium," and "high" performance). Alternatively, the geographic region performance values can be the normalized parameter values. In one example, normalizing compares corn image elements (e.g., pixels or regions) to corn image elements, while wheat image elements are compared to wheat image elements, even though the wheat and corn image elements are encompassed within the same image.

The parameter values can be normalized: per image element subset, per image segment, per image pixel (e.g., where pixels can be sub-components of the image segment, or each image segment can include a set of pixels), per geographic sub-region (e.g., grid unit), or per any other suitable set of image elements. The population of image elements used to normalize the parameter value for a first image element (normalizing population) can be the population of image elements associated with the same crop type within the same image as the first image element, the population of image elements associated with the same crop type within a second image, the population of image elements associated with the same crop type within a composite image, or be any other suitable population of image elements.

In a first example, the normalizing population can be the population of pixels or other suitable image element type associated with the same crop type within the same image segment (e.g. a set of image elements) as the pixel to be normalized (first image segment). In a second example, the normalizing population can be the population of pixels within a set of secondary image segments associated with the same crop type as the pixel to be normalized, where the set of secondary image segments can be separate and distinct image segments within the same image as the first image segment. In a third example, the normalizing population can be the population of pixels within a set of secondary image segments associated with the same crop type as the pixel to be normalized, where the set of secondary image segments can be separate and distinct image segments identified within a set of secondary images. Each secondary image segment can represent the same geographic sub-region (e.g., where the first and second images overlap) as that of the first image segment, or represent a different geographic sub-region. Each secondary image segment can be within a predetermined pixel distance from the pixel to be normalized, represent a second geographic sub-region within a predetermined geographic distance from the first geographic sub-region represented by the first image segment, be an image segment representing a geographic sub-region associated with a common user (e.g., farmer) as the geographic sub-region represented by the first image segment, be an image segment representing a geographic sub-region associated with a different user (e.g., farmer) from the geographic sub-region represented by the second image segment, or be any other suitable second image segment.

In a first specific example, the WDRVI value for a first pixel associated with corn is normalized based on the WDRVI values for remaining pixels from the subset of image elements defined in S140 (e.g., image elements from the same image segment, all corresponding to corn). In a second specific example, the NDVI value for a first pixel associated with corn is normalized based on the NDVI values for secondary pixels from the same image that are also associated with corn. In a third specific example, the WDRVI value for the first pixel associated with corn is normalized based on the WDRVI values for secondary pixels from a second image, captured at substantially the same time and representing a different geographic region from that represented by the image containing the first pixel. The different geographic region can be part of the same field as the first geographic region, or can be part of a different field. In a fourth specific example, the WDRVI value for a first grid unit associated with corn is normalized based on WDRVI values for grid units cooperatively forming the corn field with the first grid unit. In a fifth specific example, the NDVI value for a first grid unit associated with corn is normalized based on WDRVI values for other corn fields recorded at substantially the same time as the image used to determine the NDVI value for the first grid unit. The other corn fields can be owned by the same farmer, owned by different farmers, located within a threshold geographic distance of the first corn field, or be any other suitable corn field.

Normalizing the image element values can include determining a percentile ranking of a vegetative performance value relative to remaining vegetative performance values of the subset of vegetative performance values, but the image element value can be otherwise normalized. In this variation, the percentile ranking can be determined based on the ranking of vegetative performance values from comparing the vegetative performance value to a reference vegetative performance value S145. However, normalization can additionally or alternatively be based upon any other suitable type of ranking or comparison of vegetative performance values in relation to one another. The percentile is preferably determined relative to the normalizing population, but can be otherwise determined. In one example, the image element can be a first pixel of a first image, while the normalizing pixel population is the remainder of the subset to which the image element belongs. Normalizing the parameter value for the first pixel can include determining which percentile the first pixel's parameter value falls into, relative to the parameter values of the normalizing pixel population. Alternatively, normalizing the image element values can include determining the probability of each image element's parameter value, given the parameter value distribution of the normalizing population. The probability can subsequently be used as the normalized value, or be used in any other suitable manner. However, the image element values can be otherwise normalized.

2.2.F.ii Identifying and/or Removing Outliers.

In a second variation, generating geographic region performance values S150 can include identifying and/or removing outliers. In one example, outliers can be identified within the normalizing population. Outliers can result from mislabeled geographic sub-regions (e.g., where a portion of a corn field is accidentally recorded as growing wheat), mistreatment of the geographic sub-region (e.g., where a portion of the corn field is accidentally over-fertilized), or result in any other suitable manner. Outliers can be identified as image elements having values falling within a predetermined percentile (e.g., within the 20th percentile), values falling outside a predetermined percentile (e.g., above the 90th percentile, etc.), values falling outside a predetermined percentile range, values below a threshold probability of occurrence (e.g., below 40% probability of occurrence), normalized values below a threshold probability of occurrence given the normalized values of the pixel's neighbors, or be identified in any other suitable manner.

Subsequent to identification of outliers, the outliers can be removed from the normalizing population, such that the respective parameter values do not affect (e.g., skew) the normalization. Outlier removal can continue until a threshold variance within the normalizing population is achieved, until a minimum number of image elements has been reached, or until any other suitable cessation event occurs. The outlying image element can additionally or alternatively be flagged and removed from subsequent iterations of the method (e.g., for a second time duration). The crop corresponding to the outlying image element can additionally or alternatively be determined (e.g., based on parameter comparison with adjacent image elements, received from a user, etc.) and stored in association with the image element. The respective parameter value for the previously outlying image element can additionally or alternatively be included in the normalizing population for the newly determined crop categorization. However, outliers can be otherwise determined and processed.

2.2.F.iii Generating a Geographic Region Performance Map.

In a third variation, generating geographic region performance values S150 can include associating the geographic region performance values with the geographic location corresponding to each image element, thereby providing a map of geographic sub-regions and/or regions associated with metrics of relative performance. The resolution of the resultant map is preferably based on the resolution of the image element, but can alternatively be higher or lower. The resolution can be substantially constant across the map or be variable. In one example, the resolution of the resultant map can be the real-world geographic area represented by a pixel of the image. In another example, the resolution of the resultant map can be based on the image segments. However, the resolution can be otherwise determined. In one variation of the method in which the image element is an image pixel, associating the geographic region performance values with geographic locations includes determining a set of real-world geographic locations represented by the pixel (e.g., a geographic region, a geographic identifier for the geographic region, a geographic location within the geographic region, etc.) and assigning the geographic region performance value (e.g., value percentile, value probability, etc.) to the set of real-world geographic locations within a database or other storage system. However, the geographic region performance values can be otherwise associated with geographic locations and/or regions.

2.3 Generating a Geographic Region Performance Summary Map.

As shown in FIGS. 2C-5, generating a geographic region performance summary map S160 functions to generate a virtual model indicative of the expected performance for each geographic sub-region of the geographic region during one or more recurring time units. The geographic region performance summary map is preferably generated based on the geographic region performance maps for a recurring time unit across multiple time durations (e.g., all performance maps for August, across multiple years), but can alternatively be generated based on the geographic region performance maps for all time units within a time duration (e.g., all performance maps for all months within a year), or be generated based on any other suitable set of performance maps. A single geographic region performance summary map is preferably generated for a given geographic region, but any suitable number of performance maps can be generated for the geographic region. For example, different summary maps can be generated to measure different performance metrics (e.g., a map tailored to measure performance of a specific seeding prescription, a map tailored to measure yield performance generally, etc.). However, any number or type of geographic region performance summary maps can be generated for any number of geographic regions. A generated geographic region performance summary map can be updated with a new geographic region performance map. For example, the method 100 can include receiving a new image corresponding to the geographic region, generating a new geographic region performance map for the new image, and generating an updated geographic region performance summary map by combining the geographic region performance summary map with the new geographic region performance map.

Generated geographic region performance summary maps can be stored and thereafter used as a baseline for comparison with newly generated geographic region performance maps or geographic region performance summary maps. Additionally or alternatively, the geographic region performance summary maps can be used in enabling growth stage prediction of crops in field segments. The geographic region performance summary maps can additionally or alternatively be used in any manner analogous to those disclosed in U.S. application Ser. No. 15/012,738 filed 1 Feb. 2016 and titled "SYSTEM AND METHOD FOR CROP HEATH MONITORING", and to those disclosed in related U.S. application Ser. No. 15/012,749 filed 1 Feb. 2016 and titled "GROWTH STAGE DETERMINATION SYSTEM AND METHOD", which are herein incorporated in their entirety by this reference.

In a first variation, generating the geographic region performance summary map S160 includes combining a set of geographic region performance maps (e.g., maps with normalized performance values for each of a set of geographic sub-regions), but can be otherwise generated. Combining the set of geographic region performance maps can include combining a current geographic region performance map with at least one historic geographic region performance map for the same geographic region. However, any number of geographic region performance maps can be combined. Alternatively, combining geographic region performance maps can be omitted.

Combining geographic region performance maps S160 preferably includes combining individual geographic region performance maps for the geographic region corresponding to related time units (e.g., across multiple time durations). The time unit can be days, weeks, months, years, growing season, or any other suitable time unit. In a first example, geographic performance maps for August can be combined across multiple years. In a second example, geographic performance maps for the first week of July can be combined across multiple years. In a third example, geographic performance maps for all months within a year can be combined. However, the geographic performance maps can be otherwise combined. The geographic region performance maps can be combined can be on a per-image element basis (e.g., per-pixel, per-image segment, per-image, etc.), per geographic area basis (e.g., per-geographic sub-region, per geographic region, etc.), or any other suitable basis. Performance values for the same geographic sub-region are preferably combined, but performance values for different geographic sub-regions can alternatively be combined. However, selection of geographic region performance values to combine can be based on any suitable characteristics (e.g., crop type, soil characteristics, weather characteristics, geographic region performance values, vegetative performance values, etc.) or criteria. Performance values of the geographic region performance maps can be smoothed before or after combining maps. Smoothing techniques that can be performed include: linear filtering, adaptive filtering, Gaussian smoothing, moving average, Laplace smoothing, exponential smoothing, and/or any other suitable type of smoothing.

In a first variation, a current geographic region performance map is combined with a historic geographic region performance map. In a first example, the first geographic region performance map corresponds to a first instance of a first recurrent time unit in a first time duration (e.g., February of the current calendar year), and the historic geographic region performance map corresponds to a second instance of the first recurrent time unit in a second time duration (e.g., February of a previous calendar year). In an illustration of the first example, a first geographic region performance map corresponding to January of 2015 can be combined with a second geographic region performance map corresponding to January of 2016.

Figure 3:
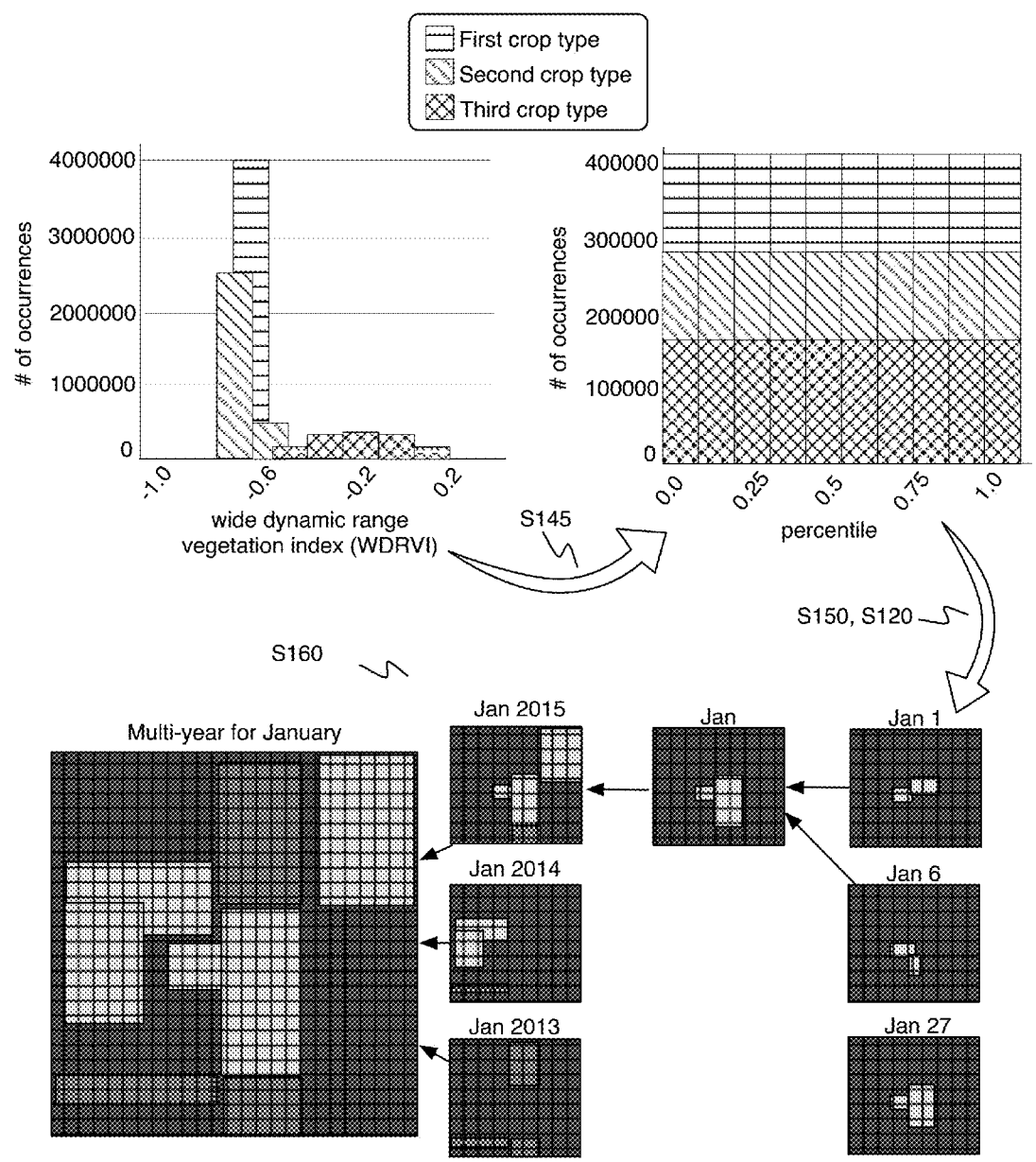
FIG. 3 is a schematic representation of a specific example of parts of the method as applied to a data set.

As shown in FIGS. 2-4, in a second example, geographic region performance maps can be combined to generate a geographic region performance summary map for a time unit within a time duration. In an illustration of the second example, the first geographic region performance map can be generated from an image captured on July 16 of the current growing season, the second geographic region performance map can be generated from an image captured on July 13 of the current growing season, and the two geographic region performance maps can be combined to generate a geographic region performance summary map for July of the current growing season. The current geographic region performance summary map can be combined with a historic geographic region performance summary map for July of the previous growing season. In a third example, representative geographic region performance summary maps for a recurrent time unit (e.g., July) within a current growing season can be combined with each available historic geographic region performance summary map for the recurrent time unit within previous growing seasons, thereby generating a multi-year performance map for the recurrent time unit.

In a second variation, geographic region performance maps corresponding to substantially the same time unit can be combined. For example, combining geographic region performance maps can include combining maps measuring different performance characteristics of the same geographic region at substantially the same time. In another example, geographic region performance maps covering overlapping but different geographic regions at substantially the same time can be combined. However, combining as in S160 can include combining any suitable geographic region performance maps covering any suitable geographic regions at any suitable time units. Combining geographic region performance maps preferably includes combining geographic region performance values of the geographic region performance maps. Additionally or alternatively, the combination of geographic region performance maps can include the combination of vegetative performance values, combined geographic region performance values, normalized parameter values, and/or pixel values, but can include processing with any other suitable data.

In a third variation, geographic region performance maps corresponding to time units within the same time duration can be combined to generate a geographic region performance summary map for the time duration. For example, all geographic region performance maps for the geographic region recorded during 2015 can be combined to create a geographic region performance summary map for 2015.

In a first variation, combining the geographic region performance maps includes averaging the performance values (e.g., normalized vegetative performance values, geographic region performance values) of a first geographic performance map with geographic region performance values of a second geographic performance map.

In a second variation, combining the geographic region performance maps includes identifying the mean performance value (e.g., normalized vegetative performance value) for each geographic sub-region, across the set of geographic region performance maps.

In a third variation, combining the geographic region performance maps includes measuring the change in performance values (e.g., vegetative performance values, geographic performance values) of a first geographic region performance map with respect to performance values of a second geographic region performance map.

In a third variation, combining the geographic region performance maps includes: weighting geographic region performance values and combining the weighted geographic region performance values. Geographic region performance values can be weighted on a map basis (e.g., wherein each geographic region performance value in the map takes on the map weight), on an individual basis (e.g., wherein different geographic region performance values within the same map have different weights), or on any other suitable basis. Geographic region performance values associated with a higher confidence level of accuracy (e.g., of the underlying data) can be weighted more heavily than geographic region performance values associated with a lower confidence level. Confidence level can be determined based on image quality, weather conditions, soil conditions, and/or any other suitable characteristic. For example, if a first geographic region performance map corresponds to a time unit at which abnormal weather conditions were present, then geographic region performance values of the first geographic region performance map can be weighted less relative to geographic region performance maps corresponding to time units associated with normal weather conditions. Alternatively, geographic region performance values can be weighted based on temporal criteria. For example, geographic region performance values associated with a time unit closer to a present time can be weighted more heavily than geographic region performance values associated with a time unit further in the past. However, the weightings can be determined in any suitable manner and/or upon any suitable criteria.

However, the geographic region performance maps can be otherwise combined.

In a second variation, generating the geographic region performance summary map for a geographic region for a recurrent time unit includes: identifying images of the geographic region recorded during the recurrent time unit (e.g., across multiple time durations); determining the vegetative performance value for each geographic sub-region represented by an image element of the identified images; combining the vegetative performance value for each geographic sub-region across the multiple time durations; and normalizing the combined vegetative performance values across the set of geographic sub-regions. However, the geographic region performance summary map can be otherwise generated.

2.4 Generating a Crop Input Prescription.

As shown in FIGS. 4 and 5, the method 100 can additionally or alternatively include generating a crop input prescription S180, which functions to enable variable rate crop treatment and management. The crop input prescription (generating a crop treatment prescription) can be based on any number of geographic region performance summary maps generated as in S160. Additionally or alternatively, generating a crop input prescription S180 can be based on the individual geographic region performance maps generated as in S120, vegetative performance values of the geographic region, soil data (e.g., soil texture, soil hydraulic properties, soil organic matter, etc.), weather data (e.g., daily temperature, precipitation, radiation, etc.), user-inputted information, and/or crop management data (e.g., user-inputted data, historic seeding prescriptions, etc.). However, any suitable type of information can be used in generating the crop input prescription S180. The crop input prescription can enable a crop type input (e.g., seeding, fertilizer, fungicide, etc.) to be variably applied with respect to time and location, but the prescription can enable the input to be variably applied with respect to any other suitable criteria. The crop input prescription can vary aspects of crop input application based on variance in geographic region performance indicated by geographic region performance summary maps, but the prescription can additionally or alternatively be varied with respect to variance in any other suitable characteristic associated with the geographic region. The application of the crop input is preferably capable of being varied at least at the granularity level of the land dimensions corresponding to an image element of the image. For example, if a geographic region corresponds to 5 square meters of a field, and an image element corresponds to 0.1 square meters of the field, the crop input prescription can preferably vary application of the crop input at the resolution of at least 0.1 square meters. However, the crop input prescription can vary crop input application at any suitable granularity level (e.g., with respect to distance, geographic region, geographic sub-region, image elements, etc.). Generation of a crop input prescription S180 can additionally or alternatively be based on user-selected preferences (e.g., types of crop input, supply of crop input, preferred range of amount of crop input application, preferred times of crop input application, etc.). For example, a user can input an amount and type of seeding supply available, and a crop input prescription can be generated in accordance with the user-inputted limitations. Alternatively, a crop input prescription can be generated independent of user input. Types of crop input prescriptions can include seeding prescriptions, fertilizer prescriptions, and/or fungicide prescriptions, but can typify any suitable type of crop input prescription. Generating a crop input prescription can include communication with components (e.g., seeding machinery) to apply the crop input prescription. Additionally or alternatively, the crop input prescription can be sent to a user at a user device. However, the crop input prescription can include communication to any suitable entity in any suitable fashion.

In a first variation, generating a crop input prescription S180 includes generating a seeding prescription. The seeding prescription can include a variable seeding rate based on the variable performance of geographic sub-regions as indicated by, for example, a geographic region performance summary map. For example, a certain type of seed and/or seeding rate can be prescribed for higher performing geographic sub-regions, and a different type of seed and/or seeding rate can be prescribed for lower performing geographic sub-regions, in order to account for variations in soil productivity. Seeding rate can be formulated in units of seeds/acre, seed cost/acre, breakeven bushels/acre, and/or any other suitable units of measurement. Additionally or alternatively, the seeding prescription includes a variable seed type based on crop type corresponding to a geographic sub-region, performance of the sub-region, and/or any other suitable criteria. However, the seeding prescription can prescribe seeding input with respect to any suitable criteria.

In a second variation, generating a crop input prescription includes generating a fertilizer prescription. The fertilizer prescription can include a nitrogen prescription, but can additionally or alternatively include a phosphorous prescription, a potassium prescription, and/or any other suitable type of fertilizer prescriptions.

2.6 Notifying a User.

As shown in FIGS. 4 and 5, the method 100 can include notifying a user S190, which functions to inform a user of a crop input prescription and/or performance indicators of the geographic region. Notifying a user S190 can be in response to generating the geographic region performance summary map as in S160, and/or in response to generating the crop input prescription as in S180. However, notifying the user S190 can be performed prior to or after any suitable part of method 100. Notifying the user S190 can include presenting the user with the geographic region performance summary map, the crop input prescription, individual geographic region performance maps, geographic region performance values, vegetative performance values, and/or any other suitable type of data. The user is preferably notified at a user device (e.g., mobile device, laptop, tablet, etc.) of the user, but can be notified through any other means. In a specific example, the notification can include treatment mechanism control instructions to achieve the crop input prescription. The notification can be sent to the treatment mechanism, wherein the treatment mechanism executes or is otherwise controlled based on the control instructions. The content of the notification is preferably tailored to preferences selected by the user. Alternatively, the notification content can be determined irrespective of any user input, but can otherwise be determined. The notification is preferably communicated to the user device by a remote server. However, any suitable entity can notify the user at any suitable device or through any suitable means.

2.6 Iterative Method Performance.

Parts of the method 100 can additionally be repeated for each of a plurality of images of substantially the same geographic region, where the plurality of images are recorded at different recurrent time units time duration. In one example, this can include repeating the method for each of a plurality of images of the geographic region, where each image of the plurality is taken at a different time within a growing season.

In a first variation, repeating the method for images of the geographic region recorded over the time duration can function to provide a measure of the region's performance pattern over the time duration (e.g., region's performance at different time units within the time duration). For example, this can provide a measure of how well the soil performs in May versus its performance in June. This information can be used to prescribe treatments to accommodate for the anticipated performance changes (e.g., plan to rent nitrogen application systems to augment the upcoming performance decrease next month), plan crop treatment schedules (e.g., planting, harvesting, fertilizing schedules, etc.), or be used in any other suitable manner.

In a second variation, repeating parts of the method for images of the geographic region recorded over the time duration can additionally function to provide additional input into the region's overall performance. For example, a high performance geographic region can perform consistently well over the growing season (e.g., consistently have vegetative performance values in the top percentile), whereas a low performance geographic region can perform well early in the growing season, but perform poorly toward the end of the growing season. In this variation, the plurality of normalized values for each image element over time can be averaged into a summary normalized value or otherwise processed to provide a time-independent performance summary map.

Parts of the method can additionally be repeated for each of a plurality of images of the same geographic region, where each of the plurality of images is recorded at substantially the same recurrent time unit across different time durations. In one example, this can include repeating the method for each of a plurality of images of the geographic region, where each image of the plurality is taken during a different time duration at substantially the same time unit within the respective time duration. In a specific example, each image can be taken during the first week different growing seasons. In a second specific example, the plurality of images includes a first image taken during May of a first year, a second image taken during May of a second year, and a third image taken during May of a third year. Repeating the method for images of the geographic region recorded at substantially the same time unit across multiple time durations can function to normalize the effects of variable factors that influence yield (e.g., differences in weather, crop type, insect and disease pressure, agronomic practices, etc.) on the performance map. Normalized values derived from images recorded during different time durations within a threshold time variation of a given time unit are preferably aggregated and processed to generate the performance summary value for each image element. For example, the normalized pixel values from images collected within a week of May 3 for each year can be aggregated and processed into the performance summary value for each pixel. The performance summary value can be the average of the normalized values across the different time durations for the image element, the mean normalized value, or be any other suitable performance summary value. However, the performance summary map can be otherwise generated.

3. Examples

In a specific example, as shown in FIGS. 2A and 2B, the method includes receiving multiple sets of images (e.g., where each set of images corresponds to images recorded in a given year). Each image set can be associated with a different time duration (e.g., a given year, a given growing season, etc.) and can include multiple subsets of images (e.g., images of multiple geographic areas or tiles, multiple images of a common geographic region where each image is recorded at approximately the same time unit in the year). Each subset of images can be captured at a different recurrent time unit (e.g., January 5) within a given time duration (e.g., captured at different time units within a given year). Each image within each image subset can be captured within a threshold time of the remainder of the subset, and each is representative of a different geographic region. Each image can be processed by determining a real-world geographic identifier for the geographic region captured by the image, identifying the pixels forming the image, and determining the vegetative performance value for each pixel of the image. The vegetative performance values of each pixel can be normalized by grouping pixels corresponding to the same type of crop (e.g., by overlaying secondary crop information over the image based on the geographic identifier, such as a cropland data layer), determining the percentile value of the vegetative performance value for each pixel based on the vegetative performance values of a representative pixel population, and using the percentile value as the normalized value for the pixel. The representative pixel population preferably includes pixels from the same image that correspond to the same crop as the pixel to be normalized, but can alternatively or additionally include pixels from the same image subset (e.g., where the images within the subset are stitched together or otherwise associated), pixels sharing the same crop and same time unit within the same time duration, or include any other suitable population of pixels. A geographic region performance map (e.g., virtual map or model of the geographic region) can be generated based on the normalized values. The geographic region performance map can be combined with a historic geographic region performance map corresponding to the same geographic region, thereby producing a geographic region performance summary map. In this example, the method 100 can additionally include summarizing the pixel value of images within a range of time units for each image set. In an illustration, all values corresponding to a predetermined growth stage (e.g., from a single image set or from multiple image sets) can be binned into a single geographic region performance map of a geographic region. In a first specific illustration, all measurements associated with a first geographic region from a first month for a first year can be binned together into a performance summary map. In a second specific illustration, all measurements associated with a second geographic region from a first month for a plurality of years can be binned together into a performance summary map.

An alternative embodiment preferably implements the above methods in a computer-readable medium storing computer-readable instructions. The instructions are preferably executed by computer-executable components preferably integrated with a baseline performance determination system. The baseline performance determination system can include a vegetative performance value extraction system, parameter value normalization system, and a mapping system configured to map the normalized parameter value to the source geographic location. The computer-readable medium may be stored on any suitable computer readable media such as RAMs, ROMs, flash memory, EEPROMs, optical devices (CD or DVD), hard drives, floppy drives, or any suitable device. The computer-executable component is preferably a processor but the instructions may alternatively or additionally be executed by any suitable dedicated hardware device.

Although omitted for conciseness, the preferred embodiments include every combination and permutation of the various system components and the various method processes.

As a person skilled in the art will recognize from the previous detailed description and from the figures and claims, modifications and changes can be made to the preferred embodiments of the invention without departing from the scope of this invention defined in the following claims.

I claim:

1. A method for measuring performance of a geographic region, the geographic region including a set of geographic sub-regions, the method comprising:
   a) receiving a first image of a physical geographic region, the first image recorded during a recurrent time unit within a first time duration, the first image comprising an image element set;
   b) for each image element of the image element set:
      mapping the image element to a virtual representation of a geographic sub-region within the geographic region,
      determining a vegetative performance value for the virtual representation of the geographic sub-region based on a spectral signal extracted from the respective image element, and
      associating the virtual representation of the geographic sub-region with a crop type from a set of crop types;
   c) identifying a first crop set comprising virtual representations of geographic sub-regions associated with a first crop type of the set of crop types;
   d) determining a first normalized vegetative performance value set, comprising determining a normalized vegetative performance value for each virtual representation of a geographic sub-region within the first crop set;
   e) generating a geographic region performance summary map for the geographic region for the recurrent time unit;
   f) generating a crop treatment prescription based on the geographic region performance summary map; and
   g) wirelessly sending the crop treatment prescription to a crop treatment system, wherein the crop treatment system is controlled based on the crop treatment prescription.

2. The method of claim 1, further comprising: wherein generating the geographic region performance summary map for the geographic region for the recurrent time unit comprises generating the geographic region performance summary map based on the first normalized vegetative performance value set and a second normalized vegetative performance value set associated with the recurrent time unit within a second time duration.

3. The method of claim 2, wherein the second normalized vegetative performance value set comprises a second normalized vegetative performance value for each virtual representation of a geographic sub-region, wherein generating a geographic region performance summary map comprises, for each virtual representation of a geographic sub-region, combining the respective normalized vegetative performance value with the respective second normalized vegetative performance value.

4. The method of claim 3, wherein the second normalized vegetative performance set is determined by performing a) to d) for a second image recorded during the recurrent time unit within the second time duration.

5. The method of claim 3, wherein a virtual representation of a geographic sub-region of the first crop set is associated with a second crop type for the recurrent time unit within the second time duration, wherein the second crop type is different from the first crop type.

6. The method of claim 5, wherein determining the normalized vegetative performance value for each virtual representation of a geographic sub-region within the first crop set comprises normalizing the respective vegetative performance value against the vegetative performance values of remaining virtual representations of geographic sub-regions of the first crop set, wherein the second normalized vegetative performance value for each virtual representation of a geographic sub-region is determined by normalizing a second vegetative performance value for the respective virtual representation of the geographic sub-region against vegetative performance values of remaining virtual representations of geographic sub-regions of a second crop set, wherein virtual representations of geographic sub-regions within the second crop set are associated with the second crop type.

7. The method of claim 2, wherein the first and the second time durations are a first and a second growing season, respectively.

8. The method of claim 1, wherein determining a normalized vegetative performance value for each virtual representation of a geographic sub-region within the first crop set comprises: normalizing the respective vegetative performance value against the vegetative performance values of remaining virtual representations of geographic sub-regions of the first crop set.

9. The method of claim 8, wherein normalizing the respective vegetative performance value comprises determining a percentile of the respective vegetative performance value relative to the vegetative performance values of remaining virtual representations of geographic sub-regions of the first crop set.

10. The method of claim 1, wherein the vegetative performance value comprises a wide dynamic range vegetation index (WDRVI) value.

11. The method of claim 1, wherein associating the virtual representation of the geographic sub-region with a crop type comprises associating the crop type with the virtual representation of the geographic sub-region based on a predetermined map of crop types for the geographic region.

12. The method of claim 11, wherein associating the virtual representation of the geographic sub-region with the crop type based on the predetermined map comprises:
receiving a crop type user input comprising the crop type associated with a geographic area encompassed by the geographic region, and
associating the crop type with virtual representations of the geographic sub-regions encompassed by the geographic area.

13. A method for measuring performance of a geographic region from a first image including an image element set, the method comprising:
receiving the first image corresponding to a first time unit;
generating a first geographic region performance map for the first image, comprising:
mapping the image element set to geographic sub-regions of the geographic region,
generating a set of vegetative performance values for the set of image elements,
determining a crop type for each image element of the image element set,
defining a first subset of the image element set, the image elements within the first subset sharing a common crop type,
generating geographic region performance values for each image element within the first image element subset, based on the vegetative performance values associated with the respective image element;
generating a first geographic region performance map based on the geographic region performance values;
generating a first geographic region performance summary map based on the first geographic region performance map and a second geographic region performance map corresponding to a second image of the geographic region, wherein the second image corresponds to a second time unit;
generating a crop treatment prescription based on the first geographic region performance summary map; and
wirelessly sending the crop treatment prescription to a crop treatment system, wherein the crop treatment system is controlled based on the crop treatment prescription.

14. The method of claim 13, wherein generating the first geographic region performance map comprises defining a second subset of the image element set based on the crop types, and wherein the first and the second image element subsets comprise different image elements, wherein the first and second image element subsets are associated with a first and second crop type, respectively.

15. The method of claim 13, wherein generating a first geographic region performance summary map comprises averaging a first geographic region performance value with a second geographic region performance value, wherein the first and the second geographic region performance value correspond to a first and a second image element, respectively, and wherein the first and the second image element both correspond to a first geographic sub-region of the geographic sub-regions.

16. The method of claim 13, wherein the first and the second time unit are within a first growing season.

17. The method of claim 16, further comprising combining the first geographic region performance summary map with a second geographic region performance summary map generated based on a third image and a fourth image, the third and the fourth images respectively corresponding to a third and a fourth time unit within a second growing season, wherein the first and the second time unit correspond to a first and a second recurring calendar month within the first growing season, and wherein the third and the fourth time unit correspond to the first and the second recurring calendar month within the second growing season.

18. The method of claim 13, further comprising:
receiving a new image corresponding to the geographic region;
generating a new geographic region performance map for the new image; and
generating an updated first geographic region performance summary map based on combining the first geographic region performance summary map with the new geographic region performance map.

19. The method of claim 13, wherein comparing the vegetative performance values comprises determining a percentile ranking of a first vegetative performance value relative to remaining vegetative performance values of the subset of vegetative performance values.

\* \* \* \* \*